United States Patent [19]

Yannas et al.

[11] Patent Number: 4,955,893

[45] Date of Patent: Sep. 11, 1990

[54] PROSTHESIS FOR PROMOTION OF NERVE REGENERATION

[75] Inventors: Ioannis V. Yannas, Newton; Dennis P. Orgill, Belmont; Howard M. Loree, II, Cambridge; James F. Kirk, Cambridge; Albert S. P. Chang, Foster City; Borivoje B. Mikic, Cambridge; Christian Krarup, Reading; Thorkild V. Norregaard, Winchester, all of Mass.

[73] Assignee: Massachusetts Institute of Technologh, Cambridge, Mass.

[21] Appl. No.: 327,530

[22] Filed: Mar. 23, 1989

Related U.S. Application Data

[63] Continuation-in-part of Ser. No. 191,415, May 9, 1988, abandoned.

[51] Int. Cl.$^5$ .......................... A61B 17/08; A61F 2/04
[52] U.S. Cl. ................................ 606/154; 606/152; 623/12; 128/DIG 8; 264/28; 264/41; 264/49
[58] Field of Search .................... 623/11, 12, 15, 66; 264/27, 8, 41, 49; 128/DIG 8, 334 R; 606/152, 154

[56] References Cited

U.S. PATENT DOCUMENTS

4,522,753  3/1985  Yannas et al. .................... 260/123.7

OTHER PUBLICATIONS

Orgill, D., *Partial Regeneration in Mammalian Tissues Using Polymeric Materials*, Ph.D. Thesis (Fall 1985).
Yannas, I. V. et al., *The 11th Annual Meeting of the Society for Biomaterials*, p. 146, Apr. 25-28, 1985.
Yannas, I. V. et al., *Proc. ACS Division of Polymeric Materials: Science and Engineering*, 53:216-218 (1985).
Yannas, I. V. et al., *Transactions Society Biomaterials*, vol. 9, p. 175 (1986).
Yannas, I. V. et al., *Advances in Biomedical Polymers*, C. G. Gebelein (ed.), Plenum Publishing Corporation, pp. 1-9 (1987).
Yannas, I. V. et al., *The 13th Annual Meeting of the Society of Biomaterials*, p. 6, Jun. 2-6, 1987.
Yannas, I. V. et al., *Society for Neuroscience Abstracts*, vol. 13, p. 1043, Nov. 1987.
Yannas, I. V., *Transactions of the 3rd World Biomaterials Congress*, 11:40 (1988).
Yannas, I. V., *Collagen: Biochemistry, Biotechnology and Molecular Biology*, Mimni, M. E. (ed.), CRC, Boca Raton, FL, vol. 3, pp. 87-115 (1988).
Yannas, I. V. et al., *Society of Neuroscience Abstract* (1988).
Chang, A. S. et al., *MRS, Symp. M: Biomedical Materials and Devices*, p. 341, Boston, MA, Nov. 30-Dec. 4, 1987.
Chang, A. S. et al., *Proceedings of the ACS Division of Polymeric Materials: Science and Engineering*, 59:906-910, (Fall Meeting 1988).
Lundborg, G. et al., *J. Neuropathol. Exp. Neurol.*, 41:412 (1982).
Lundborg, G. et al., *Exp. Neurol.*, 76:361-375, (1982).
De Medinaceli, L. and W. J. Freed, *Exp. Neurol.*, 81:459-468, (1983).
DeMedinaceli, L. et al., *Exp. Neurol.*, 81:469-487, (1983).
DeMedinaceli, L. et al., *Exp. Neurol.*, 81:488-496, (1983).

*Primary Examiner*—Alan W. Cannon
*Attorney, Agent, or Firm*—Hamilton, Brook, Smith & Reynolds

[57] ABSTRACT

A method for producing a biodegradable polymer having a preferentially oriented pore structure and a method for using the polymer to regenerate damaged nerve tissue is disclosed. The preferentially oriented pores are produced by an axial freezing process and serve to promote proper vascularation and regeneration of the damaged nerve. Preferably, the biodegradable polymer comprises uncrosslinked collagen-glycosaminoglycan.

34 Claims, No Drawings

PROSTHESIS FOR PROMOTION OF NERVE REGENERATION

GOVERNMENT SUPPORT

The invention described herein was supported in whole or in part by National Science Foundation Grant No. EET-8520548.

RELATED APPLICATION

This application is a continuation-in-part of U.S. Ser. No. 191,415, filed May 9, 1988, entitled "Prosthesis for Promotion of Nerve Regeneration", now abandoned.

BACKGROUND OF THE INVENTION

Trauma of nerve tissue is frequently followed by loss of sensory function or motor function. An injured nerve of the peripheral nervous system (PNS) may spontaneously regenerate and there may be recovery of function. However, recovery of function is rare following injury of the central nervous system (CNS).

Currently, nerve injury is treated by various suturing techniques in which the cut ends are carefully brought together prior to suturing. Another approach makes use of grafts or implants, referred to as nerve prostheses, which are fabricated from various materials or are harvested from the body of the patient (autografts) and are used as devices for bridging the gap between cut ends of nerve tissue. The most successful nerve grafts are the autografts. Typically, a nerve injury which is serious enough to justify the use of grafting is treated by an autograft which is surgically removed from the sural nerve.

The autografting procedure, which gives the best results compared to other grafting procedures when treating injuries of the PNS, has the disadvantage that the patient has to be surgically invaded to produce a graft of dimensions appropriate for treating the injured nerve. In several instances the sural nerve or other nerves that are commonly used as sources of grafts do not have dimensions which are appropriate for the injury. Another serious problem with the use of autografts is that their success rate when used with injury in the CNS is very low. Typically, a person with serious CNS injury, (e.g., spinal cord injury), remains paralyzed in spite of autografting. A major problem encountered in grafts at GNS lesions is that scar tissue forms at the site of the injury and advancing nerve fibers (axons) are intercepted by scar. As a result, injured and cut nerve fibers do not reconnect and function is not restored.

Studies of reconstruction of damaged nerve tissue have been described by De Medinaceli et al., in *Exp. Neurol.*, 81, 459 (1983); *Exp. Neurol.*, 81, 469 (1983); and *Exp. Neurol.*, 81, 488 (1983). These studies describe the physical and chemical factors which must be considered in order to achieve "reconnection". These studies described techniques in which substantial motor function was returned in rats following transaction and crushing of the sciatic nerve. In none of these studies, however, were severed sciatic nerve ends separated to a substantial degree prior to reconnection.

In *Neuropath. Exp. Neurol.*, 41, 412 (1982); and *Exp. Neurol.*, 76, 361 (1982), Lundborg et al. describe studies in rats in which a substantial gap was created between severed sciatic nerve ends, followed by attempts to achieve regeneration and recovery of function by unsheathing the cut ends in a silicone tube. Partial regeneration was found for 6 mm and 10 mm gaps, however, none was found for gaps of approximately 15 mm.

Thus, a need still exists for a method by which severed nervous system tissue can be regenerated across a substantial gap. Additionally, the regenerated nerve tissue should have the ability to restore motor function in the affected extremities.

SUMMARY OF THE INVENTION

This invention pertains to a method for producing an implant useful for the repair and regeneration of damaged nerve tissue. More particularly, this invention pertains to a method for producing a porous, biodegradable template for axonal regeneration of nerve tissue having preferentially oriented pores. According to the method, an aqueous suspension of a biodegradable polymer is introduced into a tubular mold. Preferably, the biodegradable polymer comprises collagen-glyosaminoglycan which is either crosslinked or un-crosslinked. The suspension contained within the mold is axially frozen along the mold to provide preferentially oriented aqueous phases within the frozen suspension. The frozen suspension is then exposed to a vacuum under conditions which cause the remaining aqueous phases to sublime, thereby forming a porous biodegradable template having a preferentially axially oriented pore structure. The resulting biodegradable template having preferentially oriented pores can be used as an implant or prosthesis for axonal regeneration and repair of severed nerve tissue.

In one embodiment, the biodegradable regeneration template comprises a tube with an internal diameter large enough to contain a stump of severed nerve tissue and a porous, cylindrical plug of a collagen-containing composite contained within the tube, the pores of the plug being preferentially oriented by an axial freezing process during production of the plug.

This invention further pertains to a prosthetic device for axonal regeneration of nerve tissue comprising a biodegradable polymer, such as collagen-glyosaminoglycan, having preferentially oriented pores wherein the pores are uniform throughout the polymer and have an average diameter of about 10 $\mu$m to about 80 $\mu$m.

The prostheses prepared by the methods of this invention can be used to regenerate damaged nerve fibers having a large gap distance between the severed nerve endings since the prostheses can be fabricated to desired length specification. Thus, the use of autografts to repair severed nerves is eliminated. Nerve regeneration over such large distances is feasible since the prostheses encourage directed vascularization, via preferentially oriented pores along the direction of the nerve axis rather than in a random direction away from the cut end of the nerve. Further, the prostheses direct the early formation of blood vessels along the preferentially oriented pore channels of the graft which leads to the growth of primitive nerve fibers (axons) along the same direction. The resulting nerve fibers span the entire gap between the severed nerve endings.

DETAILED DESCRIPTION OF THE INVENTION

This invention is directed to a method for fabricating a biodegradable porous prosthesis for axonal regeneration of nerve tissue in which pore channels of the device are directed along the axis of the injured nerve.

The biodegradable prosthesis material can be, for example, a composite made of collagen and glycosaminoglycan (GAG). Such collagen/GAG composites have been shown to be highly useful for biochemical applications. The typical procedures that have been used in the past to prepare collagen/GAG composite materials are described in U.S. Pat. No. 4,280,954, "Crosslinked Collagen Mucopoly-saccharide Composite Materials" (Yannas et al., 1981) and U.S. Pat. No. 4,522,753, "Method of Preserving Porosity in Porous Materials" (Yannas et al., 1985) the teachings of each are herein incorporated by reference.

One method for directing the orientation of pore channel axes within the biodegradable, porous material is by controlling the properties of particles in an aqueous suspension prior to a freeze drying process. Freeze drying, also known as lyophilization, can be described as a two-step process in which a liquid, in this case an aqueous suspension of polymeric particles, is first frozen by various processes of heat removal and is then subjected to low-temperature vacuum conditions. During the first step, the aqueous phase component of the suspension freezes into ice crystals; during the second step the ice crystals sublime into the vapor phase leaving pores in the regions formerly occupied by the aqueous phase. The resulting product is a highly porous solid in which the detailed character of the pore structure depends critically on the precise conditions prevailing during the freezing step.

The orientation of the particulate aggregates in the suspension plays a significant role in the ultimate pore structure of the material. When the particles are loosely associated into random, three-dimensional networks without preferred orientation of particles toward any axis, the pore channels in the solid resulting from the freeze-drying process do not possess any preferred orientation. On the other hand if the particles in the suspension are loosely associated into highly oriented networks, the pore channels in the freeze-dried solid are preferentially oriented.

In general, pore channels which display a random orientation can be prepared by freeze drying a suspension of collagen particles which have previously precipitated out of solution by addition of one of several glycosaminoglycans (GAG) or other substances, such as acetone, which precipitate collagen out of solution. In contrast, freeze dried solids which show highly preferential orientation of pore channel structure can be prepared by freeze drying a suspension of collagen particles to which no precipitating agent has previously been added, or from which suspension the precipitating agent has been removed by a physical separation process, such as dialysis. The observed dependence of pore-structure of the freeze dried solid on the configuration of particles which are associated in the suspension prior to freezing stems from unexpected control of dendrite growth during the freezing step. Preferential growth of ice crystal dendrites along a certain axis, followed by sublimation of the dendrites provides a method useful for the formation of a solid with oriented pore channel axes.

Additionally, orientation of pore channel structure can be produced by axially freezing the suspension using a substantial temperature gradient of a well defined orientation. This can be accomplished in a variety of ways. Generally, a porous biodegradable template having preferentially oriented pores can be prepared by first introducing an aqueous suspension of a biodegradable polymer into a tubular mold such as silicone tubing. Preferably, the biodegradable polymer is an aqueous suspension of collagen-glycosaminoglycan (GAG) in which the collagen is crosslinked with GAG using crosslinking agents such as gluteraldehyde. Most preferably, the suspension comprises collagen which is not crosslinked with GAG. The aqueous suspension contained within the mold is axially frozen along the mold to form preferentially oriented aqueous phases within the frozen suspension. The frozen suspension is then exposed to a vacuum under conditions which cause the remaining aqueous phases to sublime, thereby yielding a porous biodegradable template having a preferentially oriented pore structure.

The mold can be any cylindrical material that is non-biodegradable, biocompatible and has an internal diameter large enough to house the collagen/GAG suspension and damaged nerve stumps. Preferably, the mold comprises silicone rubber tubing.

In a preferred embodiment of this invention, a cylinder of silicone rubber which has been filled with an aqueous suspension of biodegradable polymer, such as collagen/GAG particles, is progressively lowered into a cooling bath of liquid, such as silicone oil, chilled below the freezing point of the suspension, such as by chilling with liquid nitrogen. Preferably, the cooling bath is maintained at a constant temperature. Throughout the process, the cylinder is maintained in an orientation perpendicular to the plane of the liquid surface. This configuration establishes a substantial temperature gradient along the axis of the cylinder, since the bottom end is submerged in the chilled liquid while the top is in the overhead space. The frozen suspension is then exposed to a vacuum under conditions which cause the aqueous phase to sublime, thereby forming porous biodegradable template having preferential orientation of pores in the collagen/GAG along the axis of the cylinder. Preferential pore orientation and pore diameter can be achieved by regulating the progressive freezing through manipulation of three parameters in the freezing step; immersion velocity, undercooling, and collagen/GAG concentration in the suspension.

The velocity in which the filled tubes are lowered into the bath (entry velocity) determines the magnitude and direction of the dominant heat flex vector. Control of velocity is important in the formation of pore orientation since ice dendrites grow in the direction of the dominant heat flux vector. Preferably, entry velocity is between about $2.0 \times 10^{-5}$ m/s and about $10^{-4}$ m/s. Velocities below the lower limit lead to sedimentation of the suspension. The upper limit is the maximum velocity at which to maintain the freezing front at or above the bath surface to insure axial dendrite orientation.

Pore diameter is also regulated by entry velocity. When entry velocity is increased to about one m/s, the orientation of ice dendrite growth goes from axial to radial, forcing the biodegradable polymer to the center of the tubing and leading to a smaller pore diameter at the centerline than at the periphery. Pore diameter, however, is regulated not only by entry velocity but is also dependent upon the degree of undercooling.

The average pore size of the collagen/GAG matrix can be changed by varying the temperature of the cooling bath. A colder bath temperature creates a greater density of nucleation centers that quickly sublimate, leaving behind many small pores. Warmer temperatures create lower densities of nucleation centers that undergo prolonged crystal growth before sublimating, thus creating larger pores.

Undercooling is the difference ($\Delta T$) in temperature between the freezing temperature of the suspension and the cooling bath temperature. Undercooling is dependent on apparatus design, stability of both temperature control, and type of coolant. Velocity and $\Delta T$ act in concert to determine the crystalline orientation of ice dendrites and pore diameter. For example, a large pore diameter is obtained using slow cooling rates (low V and low $\Delta T$). Likewise, a small pore diameter is obtained through rapid cooling (high V and high $\Delta T$).

The concentration of collagen/GAG within the mold can be varied to change the pore wall texture from fibrillar to lamellar as the concentration is increased. Changes in concentration, however, do not effect pore diameter. Preferably, collagen/GAG concentration in suspensions ranged between about 0.12% w/w to 0.96% w/w to insure a continuous collagen/GAG matrix.

Pore orientation can be predicted by the use of a dimensionless number, the Mikic number (Mi), to determine the effects of undercooling ($\Delta T$) and entry velocity (V) on dendrite orientation. The Mikic number is defined as the ratio of $t_f/t_e$ wherein $t_f$ is the time for radial freezing and $t_e$ is a characteristic entry time for the mold to pass into the cooling bath. The $t_f$ is derived from application of the Fourier law to radial freezing of the suspension in the mold. For simplicity, $t_e$ is a function of immersion velocity and an arbitrary length scale chosen to be the inside radius of the mold. The expression for Mi is $Mi = \delta_w h_{fg} rV/10 K_j \Delta T$ where $\delta_w$ is the density of suspension, $h_{fg}$ is the heat of fusion, r is the inner mold radius, and $K_j$ is the thermal conductivity of the mold.

The Mikic number determines the shape of isotherms near the freezing front. Since the dominant heat flux vector is always normal to these isotherms and ice dendrites grow along this vector. Mi can be used to predict the orientation of ice dendrites growing in the collagen/GAG suspension. For $Mi<1$ (slow cooling) the isotherms are shallow, flat paraboli. Strong axial orientation of ice dendrites results. For $Mi>1$ (rapid cooling), the isotherms are steep paraboli. Ice dendrites assume a strong radial orientation.

In experiments, pore orientation is strongly axial at $Mi=0.59$, but becomes strongly radial at $Mi=10^4$. Because the Mi number is derived from a highly simplified model, it is not possible to directly solve for T and V needed to give a particular Mi. Rather, Mi serves as a guide for choosing T and V experimentally. Pore structure, for instance, can become quite nonuniform for some combinations of $\Delta T$ and V. The shape of the freezing front and the orientation of ice dendrites may be predicted from the magnitude of Mi. Under rapid cooling conditions where $Mi>1$, the pore orientation is radial. Likewise, under slower cooling conditions ($Mi<1$) the pore orientation is axial.

Following formation of the collagen/GAG plugs they can be crosslinked. Suitable methods for crosslinking include heating under a vacuum and exposure to glutaraldehyde solutions. Such crosslinking methods have been described, for example, in U.S. Pat. No. 4,448,718 of Yannas et al., the teachings of which are incorporated herein by reference. The plugs can then be stored in the freeze-dried state until they are ready for further processing or needed for implantation. Storage in a 70/30 solution of isopropanol/water is one preferred way to store the plugs.

In particularly preferred embodiments, the composite of collagen and GAG is not crosslinked. This provides collagen/GAG lattices that can biodegrade at a faster rate than corresponding crosslinked collagen/GAG matrices. This is true because the rate of biodegradation is a function the degree of crosslinking, which is conveniently expressed as the of molecular weight between crosslinks (Mc). Typically, an untreated (uncrosslinked) collagen/GAG matrix has an average molecular weight between crosslinks of about 60 K Daltons. A corresponding crosslinked collagen/GAG matrix has an average molecular weight between crosslinks of about 12 K Daltons. Since Mc is linearly related to degradation rate, a crosslinked matrix will degrade about five times slower than an untreated matrix. Because the collagen/GAG matrix used for nerve regeneration is quite similar to the collagen/GAG sheets that are used for artificial skin, the effects of crosslinking are considered approximately equivalent.

The rate at which the polymer degrades is critical to the regeneration of damaged nerves since degradation rate can aid or hinder growth and elongation of axons between the severed nerve endings. Thus, it is preferable for the prosthesis to be made of polymeric materials that degrade at a rate which will not inhibit axon vascularization.

In both of the above processes, the collagen plug, either crosslinked or uncrosslinked, is intended to encourage vascularization, thereby allowing healthy nerve regeneration. The preferentially oriented pores of the plug will have a mean diameter of approximately from about 10 $\mu$m to about 300 $\mu$m. Preferably, the mean pore diameter is from about 10 $\mu$m to about 80 $\mu$m. A pore diameter of about 10 $\mu$m is most preferred. Also, the mean molecular weight between crosslinks ($M_c$) in the matrix will ideally be between from about 10,000 to about 20,000.

In yet another embodiment of the invention, the silicone rubber cylinder is replaced with a cylinder fabricated from a collagen-GAG crosslinked network. Such a cylinder ideally will have a mean pore diameter below approximately 5 $\mu$m and a low level of crosslinking. A cylinder constructed to these specifications will discourage undesirable vascularization.

Regeneration templates having oriented pore structures produced in a commercial lyophilization apparatus have been studied clinically in rats. The following examples are intended to more fully illustrate the invention.

EXAMPLE 1

Fabrication and Performance of a Biodegradable Nerve Prosthesis

Bovine Hide Collage (large-scale preparation routinely used for fabrication of devices)

A large-scale insoluble collagen preparation was supplied by the Eastern Regional Research Center, U.S. Department of Agriculture, Philadelphia, Pa. This preparation, started with fresh, uncured cowhides, flesh splits of which were subjected to liming. Treatment of cowhide with lime under mild conditions does not convert collagen to gelatin but, instead, depolymerizes collagen, apparently by scission of intermolecular crosslinks. Limed hides were fed into a strip cutter (Taylor-Stiles Model 115, Arthur G. McKee, Riegelsville, N.J.)

and, subsequently, into a rotary knife cutter (Model 910, Arthur G. McKee, Riegelsville, N.J.). This treatment reduced the hides to small thin pieces. The alkaline hide pieces (pH 12.5) were contacted over a period of 4 hr with three washes of water containing 0.3 wt % propionic acid and 0.1 wt % benzoic acid. Propionic acid (pKa 4.9) acts as a buffer and, at the end of the 4 hr contact period, reduced the pH of the slurry to a constant level (pH 5.3). Benzoic acid preserves the hide pieces in bacteriologically clean condition. The water was then separated by filtering the slurry through a three-mesh screen tray. The acidified hide pieces were fed into a high-speed disk mill (modified Robinson, Young Machinery Sales, Muncy, Pa.) and comminuted. The product of the grinding operation was frozen to −20° C. until ready for freeze drying, which yielded loose, shredded fibrous mats.

Acid Soluble Rat Tail Tendon Collagen (small-scale preparation used as internal laboratory control)

Acid soluble collagen was prepared using tails from 7-week-old female albino rats (Pel-Freeze Biologicals, Inc., Rogers, Ark.). The precise morphology of the precipitated collagen fibrils depends sensitively on the following detailed sequence of preparatory steps. All steps were carried out at 4° C. The tails were first washed with distilled water, and the tendons were removed using a pair of wire strippers. Tendon fibers were allowed to swell and dissolve for at least 24 hours in 0.05 M acetic acid solution at 4° C. The collagen dispersion was centrifuged for 10 hours at 50,000 g to separate soluble from insoluble collagen. After soluble collagen was precipitated by adding 5% (w/v) solid NaCl, the solution was allowed to stand overnight at 4° C. Precipitated collagen was pelleted by centrifugation at 2,000 g for 10 minutes at 4° C. and redissolved in 0.05 M acetic acid solution. Centrifugation at 50,000 g for 1 hour removed any insoluble material. Soluble collagen was twice reprecipitated, centrifuged at 2,000 g, redissolved, centrifuged at 50,000 g, and then dialyzed versus 0.2 M $Na_2HPO_4$. The precipitate was centrifuged at 2,000 g for 10 minutes, washed with distilled water, lyophilized, and stored at 4° C.

Chondroitin 6-sulfate

The glycosaminoglycan (GAG) used in this work was chondroitin 6-sulfate from shark cartilage (sodium salt, Type C, Sigma Chemical, St. Louis, Mo.) It was used as received, without further purification, thereby containing 2.66%-wt. nitrogen. 37.2%-wt. glucuronic acid and 5.6% wt. moisture (manufacturer's data). The intrinsic viscosity in 0.06 M phosphate buffer was 0.97 dl/g. The observed value corresponds to an approximate viscosity average molecular weight of 23,000. Chondroitin 6-sulfate is essentially an alternating copolymer of D-glucuronic acid and of an O-sulfate derivative of N-acetyl-D-galactosamine.

Bridge Fabrication

Insoluble particles of bovine hide collagen were dispersed in 0.05 M acetic acid pH 3.0. An acetic acid solution, (pH about 3.0), of chondroitin-6-sulfate, (concentration of about 8% by weight), was added dropwise to the stirred collagen suspension until a desired collagen/GAG ratio of about 90:10 was reached. GAG addition caused precipitation of collagen out of the acid medium into a fibrous mass which was homogenized.

Cylindrical collagen/GAG plugs were fabricated by filling a 25 mm length of transparent silicone tubing, internal diameter 1.5 mm (Dow Corning, Midland, Mich.), with a 0.48% w/w aqueous suspension of the collagen/GAG polymer described above. The filled tube was then placed on the shelf of a freeze dryer (Freezemobile, Virtis Corporation, Gardner, N.Y.) and a highly porous collagen/GAG plug was prepared thereby using a temperature gradient to induce a preferential orientation of pore channel axes along the axis of the tube.

This preferential pore orientation was achieved by holding the filled tube on the freeze dryer shelf with the axis of the tube oriented normal to the plane of the shelf. The chilled shelf served as a better heat transfer medium than the surrounding chilled atmosphere, thereby establishing a freezing gradient on the filled tube. This freezing gradient produced a progressive freezing along the tube which proceeded vertically upward from the surface of the tube in contact with the freeze dryer shelf. The axial freezing yielded ice crystal dendrites having a pore orientation parallel to the axis of the silicone tube.

Freeze-dried plugs were then lightly cross-linked by a dehydrothermal treatment which comprised maintaining the plugs at a temperature of about 105° C. and a pressure of about 100 mTorr for about 24 hours. This step amounted to a first antibacterial treatment. The plugs were then immersed for about 24 hours in a glutaraldehyde bath at about 21° C., which contained about 0.25% glutaraldehyde by weight in a 0.05 M acetic acid solution. This process provided additional crosslinking and simultaneously served to subject the material to a second anti-bacterial treatment. This was followed by an exhaustive rinsing in sterile, deionized water to remove traces of free glutaraldehyde. The plugs, at this point, were stored in 70/30 isopropanol/water until they were used in further processing or implantation.

Prior to implantation, 5 mm of the collagen/GAG plug was removed from each end of the tube, using microforceps, to allow space for insertion of the severed nerve ends. The polymeric plugs were studied by use of scanning electron microscopy, measurement of the average weight between crosslinks and confirmation of the fully native content of collagen was obtained using infrared spectroscopy.

In Vivo Study

Adult male rats (Wistar, approx. 300 g) were anesthetized with sodium pentobarbital. A 2 cm skin incision was made parallel and just posterior to the right femur. The avascular intermuscular plane between vastus lateralis and hamstring muscles was entered and followed to the loose fibroareolar tissue surrounding the sciatic nerve. The loose tissue was divided longitudinally thereby freeing the sciatic nerve over its full extent without devascularizing any portion. The sciatic nerve was sharply divided with microscissors. The proximal and distal nerve ends were abutted against a collagen/GAG polymer bridge placed within a cylindrical silicone rubber tube. Three 10-0 nylon sutures through the epineurium and silicon rubber tubing secured the nerve ends in place. The length of the collagen/GAG bridge, and thus the distance between the nerve ends, was 15 mm. To provide a 15 mm sciatic nerve gap, a cross anastomosis was performed between the cut ends of the proximal left sciatic nerve and the distal rights sciatic nerve. A furrow was created in the spinal extensor muscles and the adjacent spinous process was removed. A 25 mm length of transparent silicone tube having an internal diameter of about 1.5 mm was placed in this furrow and the left proximal and right distal sciatic nerve was inserted 5 mm into the ends of the tube and fixed to it with three 10-0 nylon sutures as above. In control animals, the proximal and distal nerves were placed within a silicone rubber tube which contained no collagen/GAG bridge. After hemostasis was achieved the wound was closed with a single layer of 4-0 skin sutures. No antibiotics were administered. The procedure was performed with microsurgical technique using a surgical microscope.

Animals were perfused with mixed aldehydes at six weeks following implantation of the silicone tube implant After perfusion, the implants were removed along the proximal and distal nerve ends. The silicone tube was slit longitudinally, removed, and the tissue contained therein was post fixed with the same mixed aldehydes, processed through ethanol and embedded in Spurr's plastic. Serial thick one micrometer or ultrathin sections were cut with an MT5000 DuPont Microtome. Sections were taken from the midpoint and distal three-quarter position of the tissue bridge. One micrometer sections were stained with toluidine blue and the ultrathin sections were stained with uranyl acetate and lead citrate. Electron microscope sections of the distal three quarter point of the explanted strand were used to prepare montages at 5500x in order to resolve the unmyelinated fibers of the smallest diameter. A total of 1/20 of the cross section area of the strand was carefully inspected for uniformity of distribution (excluding the perineurium); two small areas were then picked at random and the axons were counted.

A total of 10 animals were grafted; 5 animals were implanted with test grafts and 5 were implanted with controls. At six weeks the surviving four animals from the test group and five animals from the control group were sacrificed. Inspection of the implantation site showed that migration of the stumps had occurred in one the test sites and in one of the control sites leading to a gap length of significantly less than 15 mm, while one of the control sites was infected accordingly, the latter three implants were not included in subsequent studies. In the remaining three test implants and three control implants the distance between the two cut ends was measured following explanation and was found to be $15 \pm 1$ mm.

In Vivo Study Results

In spite of substantial variability in the data, significant differences were observed at 6 weeks between test grafts and their controls. In all cases, the results were observed at the three quarter distal point of each regenerated strand.

Inspection of the morphometric data in Table 1 shows that essentially no axons were observed over the cross section of control strands. The experimental gap was not bridged in one of the control sites. In the presence of collagen/GAG polymer, the average number of mylineated plus unmyelinated axons over the cross section of the regenerated strand was about 3000 and 8000 respectively. The variability observed from one test site to the other was large.

The average cross section area of regenerated strands formed in the presence of the collagen/GAG polymer was about 0.8 mm$^2$ and was only 0.008 mm$^2$ when no collagen/GAG polymer was used (Table 1). Vascularization was present but poorly developed in the third test strand. No evidence of vascularization was observed in strands which formed in the absence of collagen/GAG polymer. Test strands contained a perineural area which was ensheathed an inner core and constituted about 38% of the total area. In contrast, control strands had no inner core but comprised only perineural tissue.

TABLE 1

MORPHOMETRIC DATA AT THE THREE-QUARTER DISTAL POINT OF 15-mm STRANDS
(6 Weeks Following Implantation)

| Total Area Cross Section mm$^2$ ±1% | Inner Core Area mm$^2$ ±5% | No. Fibers Unmyelinated ±10% | No. Fibers Myelinated ±1% | Vascularization |
|---|---|---|---|---|
| A. CONTROLS (no collagen/GAG polymer in gap) | | | | |
| 0 | 0 | 0 | 0 | None |
| 0.01 | 0 | 4 | 2 | None |
| 0.014 | 0 | 0 | 0 | None |
| B. TEST ANIMALS (gap filled with collagen/GAG polymer having preferentially oriented pores) | | | | |
| 0.31 | 0.21 | 4,575 | 1,530 | Excellent |
| 1.4 | 0.91 | 18,840 | 8,560 | Excellent |
| 0.6 | 0.32 | 450 | 0 | Poor |

A gross examination of a test and control strand provided an indication of sciatic nerve regeneration across a 15 mm gap after 6 weeks. In implants which originally contained collagen/GAG bridges with preferentially oriented pores, vascularized nerve tissue almost completely replaced the biodegradable collagen/GAG cylinder that originally bridged the experimental gap. In contrast, a control, in which no collagen/GAG bridge was used, showed only a very thin strand of nonvascularized tissue spanning the gap.

Light micrographs of a toluidine blue stained transverse section through a collagen/GAG nerve bridge ("test") were obtained. The nerve guide was fixed with mixed aldehydes, processed through ethanol and embedded in Spurr's plastic. Ultrathin sections were cut with an MT5000 Dupont Microtome. The micron section was taken from the three quarter distal end of the regenerated strand. The collagen/GAG guides were largely biodegraded by six weeks; however, very small residual strands of the collagen/GAG polymer appeared as dark wavy lines or small lobes within the section. In test grafts, large numbers of myelinated and even greater numbers of unmyelinated axons, were seen throughout the section by light microscopy and were also observed with the electron microscope. In addition to Schwann cells and axons, a number of cell types, newly synthesized collagen and other extracellular matrices were observed. Rich vascular networks were seen interspersed throughout the cross section of test grafts. Dense, multiple wrappings of elongated perineural cells occupied the periphery of test grafts.

In contrast, a light micrograph of a control (no collagen/GAG polymer used in bridge) was obtained. Specimen preparation was as previously described. The cross section area of the test specimen was found to be approximately 100 times larger than that of the control.

An electron micrograph of the regenerating nerve taken from the center of a cross section cut at the distal three quarter position of the 15 mm gap 6 weeks following grafting was obtained. Collagen/GAG polymer was used to bridge the gap at the time of grafting. Both myelinated and unmyelinated axons are present.

The control, also viewed at the center of the cross section, showed only newly synthesized collagens and an occasional fibroblast 6 weeks following grafting. In controls, no collagen/GAG polymer was present in the gap at the time of grafting.

Transmission electron microscopy of several regions in the explanted test strands showed large numbers of myelinated and even larger numbers of unmyelinated fibers throughout the cross section. In addition to Schwann cells and axons, a number of cell types, newly synthesized collagen and other extracellular matrices were observed. Rich vascular networks were seen. Dense, multiple wrappings of elongated perineural cells occupied the periphery of the test strands. Inspection at a comparable location within a control showed a very small number of axons in only one of three animals examined. Blood vessels were not observed in any of the strands recovered from the three control animals. Controls consisted almost exclusively of newly synthesized collagen fibers and fibroblasts.

These results demonstrate that highly porous, biodegradable polymers, having preferentially oriented pore structure, can be used to induce regeneration of tissues other than dermis and epidermis.

EXAMPLE 2

Regulation of Dendrite Orientation

Production of Collagen/GAG Suspension

A collagen/GAG suspension was prepared according to the methods of Yannas et al., *J. Biomed. Materials Research* 14:1980, the teachings of which are incorporated herein by reference. Specifically, fibrous freeze-dried bovine hide collagen was ground in a Wiley Mill (Arthur J. Thomas Co., Philadelphia, Pa.) with a 20-mesh screen and cooled with liquid nitrogen. The ground collagen (1.65 g) was blended with 0.5M acetic acid at 15,000 rpm (Granco Overhead Blender Granco Co., Kansas City, Mo.) for one hour at 4° C. 120 ml of 0.11% w/v Chondroitin-6 sulfate solution described in Example 1 was added dropwise to the blended collagen suspension over 15 minutes at 4° C. The resulting mixture was blended for 15 minutes at 4° C. and then centrifuged at 2,300 rpm (1300 g) for two hours at 4° C. (Damon Centrifuge Model CRU-5000 Damon International Equipment Co., Needham Heights, Mass.). The supernatant was decanted and reblended at 11,000 rpm for 15 minutes at 4° C. The resulting collagen/GAG suspension (0.48% w/w in 0.05M acetic acid) was stored at 4° C. prior/ to fabrication of a nerve bridge.

Bridge Fabrication

A 0.48% w/w collagen/GAG suspension as described in the previous section was diluted to a concentration of 0.27% w/w with 0.05M acetic acid, pH 3.0. The suspension was dearated at −30 mm Hg for 10 minutes with agitation.

Cylindrical collagen/GAG plugs were fabricated by filling a 25 mm length of medical grade silicone tubing, internal diameter 1.5 mm (Dow Corning, Midland, Mich.) with an aqueous suspension of the collagen/GAG polymer described above. A highly porous collagen/GAG plug was prepared using a temperature gradient to induce a preferential orientation of pore channel axes along the axis of the tube. This preferential orientation was achieved by lowering the filled tube into a constant temperature cooling bath with the axis of the tube perpendicular to the liquid surface.

Several collagen/GAG plugs were fabricated by varying the lowering velocity, undercooling ($\Delta T$) and collagen/GAG concentration. Table 2 shows the parameters used to prepare several nerve bridges and the effect these parameters have on dendrite orientation.

TABLE 2

| Parameters for Regulation of Dendrite Orientation | | | |
|---|---|---|---|
| Sample | Velocity (m/s) | $\Delta T$(°C.) | GG Conc. (w/w %) | Dendrite Orientation |
| 1 | $2.0 \times 10^{-5}$ | 10 | .27 | axial |
| 2 | $2.0 \times 10^{-5}$ | 40 | .27 | axial |
| 3 | $10^{-4}$ | 10 | .27 | radial |
| 4 | $2.0 \times 10^{-5}$ | 10 | .12 | axial |
| 5 | $2.0 \times 10^{-5}$ | 10 | .48 | axial |
| 6 | $10^{-4}$ | 40 | .27 | radial |
| 7 | 1 | 65 | .27 | radial |

RESULTS

Pore size and orientation were studied by cutting the bridges into longitudinal and axial cross sections and examining them in the scanning electron microscope (SEM) @20 KV, 50X magnification. Average pore diameter and orientation were calculated by computer image analysis of SEM micrographs.

By adjusting the entry velocity across the range of $2.0 \times 10^{-5}$ to $10^{-4}$ m/s and changing the undercooling ($\Delta T$) across a range of 10° to 40° C., the mean pore diameter could be varied across the range of 150 to 30 microns. In addition the dendrite orientation can be changed from axial to radial by changing the parameters. Adjusting the collagen/GAG concentration in suspension across the range 0.12 to 0.48% w/w resulted in a change of pore wall structure from fibrillar to lamellar. Collagen/GAG concentration did not affect the mean pore diameter.

EXAMPLE 3

Effects of Crosslinked and Noncrosslinked Polymers on Nerve Regeneration

Bridge Fabrication

Collagen/GAG grafts were prepared, as described in Example 2. Crosslinked collagen/GAG grafts were prepared by treating the grafts with 0.25% gluteraldehyde. The grafts were 10 mm length sections containing about 7 mg/ml collagen ensheathed by a 20 mm long, 1.5 mm ID silicone tube. Collagen/GAG matrices were characterized by the average pore diameter of a cross section. Smaller pore sizes create collagen/GAG matrices with larger available surface areas. The three pore diameters that were tested, 10 $\mu$m, 60 $\mu$m, and 300 $\mu$m, had total matrix surface areas of 1400 mm$^2$, 230 mm$^2$, and 46 mm$^2$.

Dendritic crystal formation was achieved by slowly immersing the suspension-filled tube into the cooling bath. Sublimation of these slender crystals created pores oriented longitudinally along the axis of the tubing. The immersion speed of the suspension-filled tube was adjusted to optimize dendritic growth. All of the collagen/GAG matrices had pores similarly oriented axially along the length of the tube.

A 0.25% gluteraldehyde solution was used to heavily crosslink the collagen/GAG matrix and decrease the degradation rate. To produce a collagen/GAG matrix with a slow degradation rate, a finished collagen/GAG matrix ready for implantation was immersed in the gluteraldehyde solution for 24 hours.

In Vivo Study

The sciatic nerves in adult female Sprague-Dawley rats (Charles River Laboratories, Inc., approximately 230-250 g.) were surgically transected using similar procedures as performed in Example 1. The nerve stumps were grafted together using crosslinked or non-crosslinked collagen/GAG plugs having varying pore diameters. Both plug types were 10 mm in length and ensheathed in 20 mm tubes of silicone rubber, thus providing a 10 mm separation between the nerve stumps. Empty silicon tubes and saline-filled tubes bridging similar 10 mm gaps between transected ends were grafted as controls. The grafting procedures as described in Example 1 were used. The degree of regeneration was evaluated by monitoring electrophysiological properties of the motor unit comprising the sciatic nerve and the plantar flexor muscles. Electrical stimuli were applied to the nerve, both proximal and distal to the transaction site, and the resulting compound muscle action potentials (CMAP's) elicited in the Plantar muscles of the foot were recorded. The time between the stimulation of the nerve and the onset of the elicited CMAP, termed the distal motor latency, and the CMAP amplitude from both the ankle and hip stimulations were monitored. In addition, the conduction velocity between the two sites and neuromuscular latency was computed from the measured latencies and also monitored.

In Vivo Study Results

For a period of ten weeks after the grafting operation, the rats displayed no sensory perception of electrophysiological response. The gastrocnemius had begun to atrophy, and at about six weeks post-operation the muscle has severely atrophied to the point that there remained little evidence of any muscular tissue. When a motor unit successfully regenerated, the first indications were a gradual recovery of muscle tone in the gastrocnemius and sensory perception to foot pinching. Thus, successful regeneration was considered to have occurred when at least one CMAP was observed in the plantar muscles of the foot when the nerve was stimulated from either the hip or ankle. Muscle tone correlated well with recovery, but was a difficult quantity to measure. Tests of sensory perception were difficult to perform because vocal or physical movement responses often appeared to be a result of handling the animal. Neither of these methods provided quantifiable measures of recovery and were treated only as observations. In many of the successfully regenerated motor units the toes were observed to curl inward, although none of them seemed to regain the ability to grasp with the toes. The inward curling of the toes suggests that reinnervation of the flexor plantar muscles was superior to the reinnervation of the extensor muscles.

The 27 motor units grafted with uncrosslinked collagen/GAG matrices, therefore allowing the matrices to degrade quickly, exhibited 100% successful regeneration. The 23 motor units grafted with crosslinked collagen/GAG matrices therefore decreasing the degradation rate, achieved a nearly flawless regeneration rate of 96%. Motor units that were grafted with either empty or saline-filled tubes, 21 total, displayed successful regeneration in only 29% of the cases.

Electrophysiological responses followed the qualitatively-treated observations usually within one to two weeks. The threshold levels to elicit the first signals were about 20 V approximately five times the threshold of the ungrafted controls. In each of the uncrosslinked graft groups, the first CMAP's were recorded between 12 and 13 weeks. Animals with 10 μm pore size grafts first had measurable responses around 12 weeks, while with 60 μm and 300 μm pore size grafts responses were first measured around 13 weeks. Similar results occurred when grafted with crosslinked 300 μm pore size grafts. The crosslinked 10 μm and 60 μm pore size grafts produced responses first at 16 and 17 weeks, respectively. When grafted with saline-filled tubes the first measured responses occurred around 17 weeks, while with the empty tubes the only motor unit exhibiting successful regeneration first occurred around 14 weeks. Table 3 shows the first occurrences of the earliest measured responses for each graft type. For each group the time of the first measured responses was defined as the week after transection that at least two motor units were observed to elicit a CMAP.

TABLE 3

| GRAFT TYPE | | Regeneration Success Rate % | Weeks After Transection |
| --- | --- | --- | --- |
| Pore Size (μm) | Crosslinked | (Number of Animals Tested) | of First Responses |
| 10 | No | 100 (6) | 12 |
| 60 | No | 100 (13) | 13 |
| 300 | No | 100 (8) | 13 |
| 10 | Yes | 100 (8) | 16 |
| 60 | Yes | 83 (6) | 17 |
| 300 | Yes | 100 (9) | 13 |
| Empty | — | 17 (6) | 14 |
| Saline Filled | — | 33 (15) | 17 |

There appears to be a moderate relationship between pore size and regeneration using uncrosslinked grafts. The 10 μm pore size collagen/GAG grafts exhibited better regeneration than the 60 μm grafts, which produced better regeneration than the 300 μm grafts. Both long-term distal motor latencies, both long-term CMAP amplitudes, and the long-term conduction velocity of each of these three groups show that as the pore size becomes smaller the resulting regeneration improves. This suggests that the physical pore size of the substratum affects the regeneration of nerve fibers. The 10 μm pore size matrix provides a surface area that is about six times as large as that of the 60 μm pore size matrix, which provides a surface area that is about five times as large as that of the 300 μm pore size matrix. The enhanced regeneration with the smaller pores may also be due to the larger available surface area of substratum.

Uncrosslinked collagen/GAG matrices appeared to result in regeneration that is closer to normal than the results attained with crosslinked collagen/GAG matrices. With uncrosslinked grafts the nerve regeneration was closer to normal with smaller pore sizes. The success rates of each are nearly equivalent, but motor units grafted with uncrosslinked collagen/GAG matrices were observed to elicit CMAP's earlier. In addition, the long-term distal motor latencies from both ankle and hip stimulations, conduction velocity, and CMAP amplitudes from both ankle and hip stimulations were closer to normal. As implied by the CMAP amplitudes, more axons crossed the 10 mm gap when an uncrosslinked collagen/GAG matrix was used. The higher conduction velocity and shorter distal motor latencies show that the regenerated fibers were closer to normal. Morphological observations from an earlier study of a heavily crosslinked 15 mm graft showed residual collagen/GAG remaining in the tube even after 12 weeks. These results suggest that a slowly degrading collagen/GAG matrix affects regeneration by physically impeding axonal growth and elongation, restricting the number of axons crossing a gap and limiting the level of regeneration that the axons can attain.

These results demonstrate that the degradation rate of the porous biodegradable polymers, having preferentially oriented pore structure effects the regeneration of damaged nerves.

Equivalents

Those skilled in the art will recognize, or be able to ascertain employing no more than routine experimentation, many equivalents to the specific materials, steps, etc., described above. Such equivalents are intended to be encompassed within the following claims.

We claim:

1. A prosthetic device for axonal regeneration of nerve tissue, said device comprising a porous, biodegradable template with preferentially oriented pores, made by a method comprising the steps of:
   a. introducing an aqueous suspension of collagen-glycosaminoglycan into a tubular mold;
   b. lowering the tube axially into a liquid cooling bath sufficient to freeze the suspension, the lowering being at a rate such that ice crystals oriented parallel to the axis are formed;
   c. sectioning the mold to provide at least one prosthesis;
   d. exposing the frozen material to a vacuum under conditions which cause the ice crystals to sublime, thereby forming a regeneration template with preferentially oriented pores having an average pore diameter sufficient for axonal regeneration; and
   e. providing a means for maintaining contact between the regeneration template and a nerve end.

2. A prosthetic device as claimed in claim 1 wherein the collagen-glycosaminoglycan is crosslinked.

3. A prosthetic device as claimed in claim 1 wherein the mole comprises a medical grade, silicone tube.

4. A method for axonal regeneration of nerve tissue, comprising the steps of:
   a. providing a porous, biodegradable regeneration template having preferentially oriented pores, said template made by the process comprising:
      (i) introducing an aqueous suspension of a biodegradable polymer into a tubular mold, said biodegradable polymer comprising the material of the template;
      (ii) lowering the mold axially into a liquid cooling bath sufficient to freeze the suspension, the lowering being at a rate such that ice crystals oriented parallel to the axis of the mold are formed; and
      (iii) exposing the frozen material to a vacuum under conditions which cause the ice crystals to sublime, thereby forming a preferentially oriented pore structure,
   b. contacting a severed end of nerve tissue at each peripheral end of the regeneration template, said template oriented in a manner such that the pores of the template are oriented axially with the nerve ends; and
   c. providing a means to maintain contact between the nerve ends and the regeneration template.

5. A method as claimed in claim 4 wherein the biodegradable regeneration template comprises collagen-glycosaminoglycan.

6. A method as claimed in claim 5 wherein the collagen-glycosaminoglycan is crosslinked.

7. A prosthetic device of for axonal regeneration of nerve tissue made by the method of claim 1.

8. The prosthetic device of claim 7 wherein the biodegradable polymer is contained within a tubular mold, comprising nonbiodegradable material having an internal diameter large enough to insert damaged nerve fibers therein.

9. The prosthetic device of claim 7 wherein the biodegradable polymer comprises collagen-glycosaminoglycans.

10. The prosthetic device of claim 9 wherein the collagen-glycosaminoglycan is crosslinked.

11. A method for producing a porous, biodegradable template for axonal regeneration of nerve tissue, comprising the steps of:
   a. introducing an aqueous suspension of a biodegradable polymer into a tubular mold for said template;
   b. lowering the tube axially into a liquid chilled below the freezing point of the suspension, the lowering being at a rate such that ice crystals oriented parallel to the axis are formed; and
   c. exposing the frozen suspensions to a vacuum under conditions which cause the ice crystals to sublime, thereby forming a porous biodegradable template having a preferentially oriented pore structure.

12. In the process for producing biodegradable templates for axonal regeneration of nerve tissue which comprises providing an aqueous suspension of a biodegradable, polymeric material, freezing the suspension to produce preferentially oriented ice crystals, and causing the ice crystals to sublime thereby providing preferentially oriented pores, the improvement which comprises producing the preferentially oriented ice crystals by axially immersing a mold containing the aqueous suspension in a chilled liquid, said axial immersion proceeding in a direction substantially parallel to the preferred pore orientation.

13. A method for producing a porous, biodegradable template for axonal regeneration of nerve tissue, comprising the steps of:
   a. introducing an aqueous suspension of a biodegradable polymer into a tubular mold for said template;
   b. introducing the mold into a liquid cooling bath under conditions suitable to freeze the suspension of biodegradable polymer axially along the tubular mold to provide preferentially oriented ice crystals within the frozen suspension; and
   c. exposing the frozen suspension to a vacuum under conditions with cause the ice crystals to sublime, thereby forming a porous biodegradable template having a preferentially oriented pore structure.

14. A method as in claim 13 wherein the biodegradable polymer comprises collagen-glycosaminoglycans.

15. A method as in claim 14 wherein the collagen-glycosaminoglycan is crosslinked.

16. A method as in claim 13 wherein the mold comprises a medical grade, silicone tube.

17. A method as in claim 13 wherein the aqueous suspension is frozen by axially immersing the mold in a chilled liquid.

18. A method as in claim 17 wherein the chilled liquid comprises silicone oil cooled with liquid nitrogen.

19. A method as in claim 17 wherein the chilled liquid is maintained at a constant temperature.

20. A method as claimed in claim 13 wherein the aqueous suspension within the mold is lowered into the liquid cooling bath at a rate of from about $2.0 \times 10^{-5}$ to about $10^{-4}$ m/s until said mold is completely immersed.

21. A method as claimed in claim 14 wherein the collagen-glycosaminoglycan in suspension is from about 0.12% to about 0.96% w/w.

22. A method as in claim 1 wherein the frozen suspension is exposed to a vacuum for a period of time sufficient to allow substantially all ice crystals to sublime.

23. A method for producing a porous, biodegradable template, useful for axonal regeneration of nerve tissue, comprising the steps of:
   a. introducing an aqueous suspension of a biodegradable polymer into a tubular mold for said template;
   b. introducing the mold into a constant temperature liquid cooling bath at a controlled velocity and under conditions suitable to freeze the suspension of biodegradable polymer axially along the tubular mold to provide preferentially oriented ice crystals within the frozen suspension; and
   c. exposing the frozen suspension to a vacuum, under conditions which cause the ice crystals to sublime, thereby forming a porous biodegradable template having a preferentially oriented pore structure.

24. A method as in claim 23 wherein the biodegradable polymer comprises collagen-glycosaminoglycans.

25. A method as in claim 24 wherein the collagen-glycosaminoglycan is crosslinked.

26. A method as in claim 23 wherein the mold comprises a medical grade, silicone tube.

27. A method as in claim 23 wherein the aqueous suspensions is frozen by axially immersing the mold in a chilled liquid.

28. A method as in claim 27 wherein the chilled liquid comprises silicone oil cooled with liquid nitrogen.

29. A method as in claim 27 wherein the chilled liquid is maintained at a constant temperature.

30. A method as claimed in claim 23 wherein the aqueous suspension within the mold is lowered into the liquid cooling bath at a rate of from about $2.0 \times 10^{-5}$ to about $10^{-4}$ m/s until said mold is completely immersed.

31. A method as claimed in claim 24 wherein the collagen-glycosaminoglycan in suspension is from about 0.12% to about 0.96% w/w.

32. A method of claim 23 wherein the frozen suspension is exposed to a vacuum for a period of time sufficient to allow substantially all ice crystals to sublime.

33. A method for producing a porous, biodegradable template for axonal regeneration of nerve tissue, comprising the steps of:
   a. introducing an aqueous suspension of collagen-glycosaminoglycan into a tubular mold;
   b. introducing the mold into a constant temperature cooling bath at a velocity of from about $2.0 \times 10^{-5}$ to about $10^{-4}$ m/s until the mold is completely immersed, under conditions suitable to freeze the suspension of collagen-glycosaminoglycan axially along the tubular mold to provide preferentially oriented ice crystals within the frozen suspension; and
   c. exposing the frozen suspension to a vacuum for a period of time sufficient to allow substantially all of the ice crystals to sublime, thereby forming a porous biodegradable template having a preferentially axially oriented pore structure.

34. A method as claimed in claim 33 wherein the collagen-glycosaminoglycan in suspension is from about 0.12% to about 0.96% w/w.

* * * * *

UNITED STATES PATENT AND TRADEMARK OFFICE
CERTIFICATE OF CORRECTION

PATENT NO. : 4,955,893

DATED : September 11, 1990

INVENTOR(S) : Ioannis V. Yannas, Dennis P. Orgill, Howard M. Loree, III, James F. Kirk, Albert S. P. Chang, Borivoji B. Mikic, Christian Krarup, Thorkild V. Norregaard, Nicholas T. Zervas It is certified that error appears in the above-identified patent and that said Letters Patent is hereby corrected as shown below:

Title page, under "Assignee", change "Technologh" to ---Technology---.

Title page, under "Inventors", the following inventor should be listed: ---Nicholas T. Zervas, of Milton, MA---.

Signed and Sealed this

Nineteenth Day of May, 1992

Attest:

DOUGLAS B. COMER

Attesting Officer

Acting Commissioner of Patents and Trademarks